(12) United States Patent
Lee

(10) Patent No.: US 10,995,054 B2
(45) Date of Patent: May 4, 2021

(54) HYPERPOLARIZED [3-$^{13}$C]ACETOACETATE AND METHODS OF USING THE SAME

(71) Applicant: Agency for Science, Technology and Research, Singapore (SG)

(72) Inventor: Teck Hock Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 16/345,641

(22) PCT Filed: Oct. 16, 2017

(86) PCT No.: PCT/SG2017/050518
§ 371 (c)(1),
(2) Date: Apr. 26, 2019

(87) PCT Pub. No.: WO2018/080394
PCT Pub. Date: May 3, 2018

(65) Prior Publication Data
US 2019/0270693 A1 Sep. 5, 2019

(30) Foreign Application Priority Data
Oct. 28, 2016 (SG) .......................... 10201609057Q

(51) Int. Cl.
*C07C 69/72* (2006.01)
*A61K 49/10* (2006.01)
*C07B 59/00* (2006.01)
*C07C 67/48* (2006.01)

(52) U.S. Cl.
CPC .............. *C07C 69/72* (2013.01); *A61K 49/10* (2013.01); *C07B 59/001* (2013.01); *C07C 67/48* (2013.01); *C07B 2200/05* (2013.01)

(58) Field of Classification Search
CPC ......... C07C 69/72; C07C 67/48; A61K 49/10; C07B 59/001; C07B 2200/05
See application file for complete search history.

(56) References Cited

FOREIGN PATENT DOCUMENTS

WO 2011124672 A1 10/2011
WO 2014118258 A1 8/2014

OTHER PUBLICATIONS

International Preliminary Report on Patentability for International Application No. PCT/SG2017/050518 dated Dec. 24, 2018, pp. 1-13.
Written Opinion of the International Searching Authority for International Application No. PCT/SG2017/050518 dated Jan. 5, 2018, pp. 1-5.
Extended European Search Report for European Patent Application No. 17 863 314.5 dated Jun. 5, 2020, pp. 1-10.
Jensen et al., "Hyperpolarized [1,3-13C2]ethyl Acetoacetate is a Novel Diagnostic Metabolic Marker of Liver Cancer," International Journal of Cancer, vol. 136, No. 4, 2014, pp. E117-E126.
Tyler et al., "Hyperpolarized Ketone Body Metabolism in the Perfused Rat Heart," International Society for Magnetic Resonance in Medicine, Apr. 28, 2014, p. 2769.
Russell et al., "Changes in Citric Acid Cycle Flux and Anaplerosis Antedate the Functional Decline in Isolated Rat Hearts Utilizing Acetoacetate," Journal of Clinical Investigation, vol. 87, Feb. 1991, pp. 384-390.
Balasse et al., "Evidence for a Stimulatory Effect of Ketone Bodies on Insulin Secretion in Man," Hormone and Metabolic Research, vol. 2, 1970, pp. 371-372.
Wang et al., "A General Chemical Shift Decomposition Method for Hyperpolarized 13C Metabolite Magnetic Resonance Imaging," Magn Reson Chem., vol. 54, No. 8, Aug. 2016, pp. 665-673.
Bougneres et al., "Study of Ketone Body Kinetics in Children by a Combined Perfusion of 13C and 2H3 Tracers," Am J Physiol., vol. 253, No. 5, Nov. 1987, pp. E496-E502.
Day et al., "Detecting Tumor Response to Treatment Using Hyperpolarized 13C Magnetic Resonance Imaging and Spectroscopy," Natural Medicine, vol. 13, No. 11, Nov. 2007, pp. 1382-1387.
Ball et al., "Hyperpolarized Butyrate: A Metabolic Probe of Short Chain Fatty Acid Metabolism in the Heart," Magnetic Resonance in Medicine, vol. 71, 2014, pp. 1663-1669.
Chen et al., "Metabolism of Hyperpolarized 13C-Acetoacetate/B-Hydroxybutyrate Reveals Mitochondrial Redox State in Perfused Rat Hearts," 24th International Proceedings for International Society for Magnetic Resonance in Medicine (ISMRM), May 7-13, 2016, See Abstract.
Chen et al., "Investigating In Vivo Cardiac Ketone Bodies Metabolism Using Hyperpolarized 13C Acetoacetate," 24th International Proceedings for International Society for Magnetic Resonance in Medicine (ISMRM), May 7-13, 2016, See Abstract.
Leo M. Hall, "Preparation of Crystalline Lithium Acetoacetate," Analytical Biochemistry, vol. 3, 1962, pp. 75-80.
Kennedy et al., "Detection of Hyperpolarized 13C Labeled Ketone Bodies in Vivo," Proc. Intl. Soc. Mag. Reson. Med., vol. 20, 2012, p. 4326.

(Continued)

Primary Examiner — Robert S Cabral
(74) Attorney, Agent, or Firm — Winstead PC

(57) ABSTRACT

The present invention relates to hyperpolarized [3-$^{13}$C] acetoacetate. Provided are [3-$^{13}$C]acetoacetate and compositions comprising said [3-$^{13}$C]acetoacetate. Further provided are methods of preparing and using hyperpolarized [3-$^{13}$C]acetoacetate in the determination of the spatial and temporal distribution and metabolism of [3-$^{13}$C]acetoacetate and/or its metabolites in a cell or subject, preferably by magnetic resonance imaging (MRI), magnetic resonance spectroscopy (MRS), and/or magnetic resonance spectroscopic imaging (MRSI), whereby conditions, diseases, or disorders associated with the metabolism of acetoacetate and/or other ketone bodies can be diagnosed. The conditions, diseases, or disorders to be diagnosed preferably are cancer, diabetes, cardiovascular diseases, or neurodegenerative diseases.

13 Claims, 7 Drawing Sheets

(56) References Cited

OTHER PUBLICATIONS

Hasselbaink et al., "Ketone Bodies Disturb Fatty Acid Handling in Isolated Cardiomyocytes Derived from Control and Diabetic Rats," Biochem. J., vol. 371, 2003, pp. 753-760.

Lopaschuk et al., "Myocardial Fatty Acid Metabolism in Health and Disease," Physiol Rev, vol. 90, 2010, pp. 207-258.

Lopaschuk et al., "Evolving Concepts of Myocardial Energy Metabolism: More Than Just Fats and Carbohydrates," Circulation Research, vol. 119, 2016, pp. 1173-1176.

Aubert et al., "The Failing Heart Relies on Ketone Bodies as a Fuel," Circulation, vol. 133, No. 8, Feb. 23, 2016, pp. 698-705.

Bedi et al., "Evidence for Intramyocardial Disruption of Lipid Metabolism and Increased Myocardial Ketone Utilization in Advanced Human Heart Failure," Circulation, vol. 133, No. 8, Feb. 23, 2016, pp. 706-716.

Cotter et al., "Successful Adaptation to Ketosis by Mice with Tissue-Specific Deficiency of Ketone Body Oxidation," Am J Physiol Endocrinol Metab, vol. 304, Dec. 11, 2012, pp. E363-E374.

Zou et al., "dl-3-Hydroxybutyrate Administration Prevents Myocardial Damage After Coronary Occlusion in Rat Hearts," Am J Physiol Heart Circ Physiol, vol. 283, 2002, pp. H1968-H1974.

Ziegler, et al., "Non-Invasive Measurements of Myocardial Carbon Metabolism Using In Vivo 13C NMR Spectroscopy," NMR in Biomedicine, vol. 15, 2002, pp. 222-234.

Wentz et al., "Adaptation of Myocardial Substrate Metabolism to a Ketogenic Nutrient Environment," Journal of Biological Chemistry, vol. 285, No. 32, Aug. 6, 2010, pp. 24447-24456.

Schugar et al., "Cardiomyocyte-Specific Deficiency of Ketone Body Metabolism Promotes Accelerated Pathological Remodeling," Molecular Metabolism, vol. 3, 2014, pp. 754-769.

Janardhan et al., "Altered Systemic Ketone Body Metabolism in Advanced Heart Failure," Texas Heart Institute Journal, vol. 38, Nov. 5, 2011, pp. 533-338.

Blomqvist et al., "Use of R-Beta-[1-11C]hydroxybutyrate in PET Studies of Regional Cerebral Uptake of Ketone Bodies in Humans," American Journal of Physiology-Endocrinology and Metabolism, vol. 269, 1995, pp. E948 LP-E959.

Bentourkia et al., "PET Study of 11C-Acetoacetate Kinetics in Rat Brain During Dietary Treatments Affecting Ketosis," American Journal of Physiology-Endocrinology and Metabolism, vol. 296, 2009, pp. E796-E801.

Croteau et al., "[11C]-Acetoacetate PET Imaging: A Potential Early Marker for Cardiac Heart Failure," Nuclear Medicine and Biology, vol. 41, 2014, pp. 863-870.

Ardenkjaer-Larsen et al., "Increase in Signal-to-Noise Ratio of > 10,000 Times in Liquid-State NMR," Proceedings of the National Academy of Sciences of the United States of America, vol. 100, No. 18, Sep. 2, 2003, pp. 10158-10163.

Lee et al., "In Vivo Hyperpolarized Carbon-13 Magnetic Resonance Spectroscopy Reveals Increased Pyruvate Carboxylase Flux in an Insulin-Resistant Mouse Model," Hepatology, vol. 57, Feb. 2013, pp. 515-524.

Rider et al., "Clinical Implications of Cardiac Hyperpolarized Magnetic Resonance Imaging," Journal of Cardiovascular Magnetic Resonance, vol. 15, No. 93, 2013, pp. 1-9.

Atherton et al., "The Role of PDH Inhibition in the Development of Hypertrophy in the Hyperthyroid Rat Heart: A Combined MRI and Hyperpolarized MRS Study," Circulation, vol. 123, No. 22, Jun. 7, 2011, pp. 2552-2561.

Bates et al., "Turnover Rates of Ketone Bodies in Normal, Starved and Alloxan-Diabetic Rats," Biochem J., vol. 110, 1968, pp. 655-661.

Moreno et al., "Competition of Pyruvate with Physiological Substrates for Oxidation by the Heart: Implications for Studies with Hyperpolarized [1-13C] Pyruvate," American Journal of Physiology—Heart and Circulatory, vol. 298, 2010, pp. H1556-H1564.

Naressi et al., "Java-Based Graphical User Interface for the MRUI Quantitation Package, "Magnetic Resonance Materials in Physics, Biology and Medicine, vol. 12, 2001, pp. 141-152.

Manning et al., "In Vivo Assessment of LV Mass in Mice Using High-Frequency Cardiac Ultrasound: Necropsy Validation," American Journal of Physiology, vol. 266, 1994, pp. H1672 LP-H1675.

Schneider et al., "Fast, High-Resolution in Vivo Cine Magnetic Resonance Imaging in Normal and Failing Mouse Hearts on a Vertical 11.7 T System," Journal of Magnetic Resonance Imaging, vol. 18, 2003, pp. 691-701.

Tanaka et al., "Differential Expression of Succinyl CoA Transferase (SCOT) Genes in Somatic and Germline Cells of the Mouse Testis," International Journal of Andrology, vol. 26, 2003, pp. 52-56.

Andrews et al., "Adaptive Mechanisms Regulate Preferred Utilization of Ketones in the Heart and Brain of a Hibernating Mammal During Arousal from Torpor," American Journal of Physiology-Regulatory, Integrative and Comparative Physiology, vol. 296, 2009, pp. R383-R393.

Turko et al., "Diabetes-Associated Nitration of Tyrosine and Inactivation of Succinyl-CoA:3-Oxoacid CoA-Transferase," American Journal of Physiology—Heart and Circulatory Physiology, vol. 281, 2001, pp. H2289-H2294.

Hamirani et al., "Noninvasive Detection of Early Metabolic Left Ventricular Remodeling in Systemic Hypertension," Cardiology, vol. 133, No. 3, 2016, pp. 157-162.

Sarkozy et al., "Transcriptomic Alterations in the Heart of Non-Obese Type 2 Diabetic Goto-Kakizaki Rats," Cardiovascular Diabetology, vol. 15, No. 110, 2016, pp. 1-21.

Devanathan et al., "Genomic and Metabolic Disposition of Non-Obese Type 2 Diabetic Rats to Increased Myocardial Fatty Acid Metabolism," PLOS One, vol. 8, No. 10, Oct. 2013, pp. 1-10.

Cotter et al., "Ketone Body Metabolism and Cardiovascular Disease," American Journal of Physiology—Heart and Circulatory Physiology, vol. 304, 2013, pp. H1060-H1076.

Williamson et al., "The Redox State of Free Nicotinamide-Adenine Dinucleotide in the Cytoplasm and Mitochondria of Rat Liver," Biochemical Journal, vol. 103, 1967, pp. 514-527.

Bock et al., "Preparation of a Homogeneous Soluble D-B-Hydroxybutyrate Apodehydrogenase from Mitochondria," Journal of Biological Chemistry, vol. 250, No. 15, Aug. 10, 1975, pp. 5774-5781.

Lehninger et al., "D-B-Hydroxybutyric Dehydrogenase of Mitochondria," Journal of Biological Chemistry, vol. 235, No. 8, Aug. 1960, pp. 2450-2455.

Fukao et al., "Pathways and Control of Ketone Body So Metabolism: on the Fringe of Lipid Biochemistry," Prostaglandins, Leukotrienes and Essential Fattty Acids, vol. 70, 2004, pp. 243-251.

Aon et al., "Protective Mechanisms of Mitochondria and Heart Function in Diabetes," Antioxidants & Redox Signaling, vol. 22, No. 17, 2015, pp. 1563-1586.

Zinman et al., "Empagliflozin, Cardiovascular Outcomes, and Mortality in Type 2 Diabetes," The New England Journal of Medicine, vol. 373, No. 22, Nov. 26, 2015, pp. 2117-2128.

Ferrannini et al., "CV Protection in the EMPA-REG Outcome Trial: A 'Thrifty Substrate' Hypothesis," Diabetes Care, vol. 39, Jul. 2016, pp. 1108-1114.

Mudaliar et al., "Can a Shift in Fuel Energetics Explain the Beneficial Cardiorenal Outcomes in the EMPA-REG Outcome Study? A Unifying Hypothesis," Diabetes Care, vol. 39, Jul. 2016, pp. 1115-1122.

Lopaschuk et al., "Empagliflozin's Fuel Hypothesis: Not So Soon," Cell Metabolism, vol. 24, Aug. 9, 2016, pp. 200-202.

Horton et al., "Mitochondrial Protein Hyperacetylation in the Failing Heart," JCI Insight, vol. 1, No. 2, 2016, pp. 1-14.

A

B

C

HYPERPOLARIZED [3-$^{13}$C]ACETOACETATE AND METHODS OF USING THE SAME

CROSS-REFERENCE TO RELATED APPLICATION

This application makes reference to and claims the benefit of priority of the Singapore Patent Application No. 10201609057Q filed on 28 Oct. 2016, the content of which is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates generally to hyperpolarized [3-$^{13}$C]acetoacetate and its medical applications.

BACKGROUND OF THE INVENTION

Hyperpolarized $^{13}$C magnetic resonance is an established technology for studying metabolism and hyperpolarized [1-$^{13}$C]butyrate and [1-$^{13}$C]pyruvate are among the best known non-radioactive metabolic tracers. Despite the progress made in this field, there remains a considerable need for new $^{13}$C metabolic tracers.

SUMMARY OF THE INVENTION

The present invention satisfies the aforementioned need in the art by providing hyperpolarized [3-$^{13}$C]acetoacetate and methods of preparing and using the same.

In a first aspect, the invention provides [3-$^{13}$C]acetoacetate, wherein at least 0.1%, more preferably at least 1%, and most preferably at least 10% of said [3-$^{13}$C]acetoacetate is hyperpolarized.

In a second aspect, the invention provides a composition comprising the [3-$^{13}$C]acetoacetate described herein.

In a third aspect, the invention provides a method of preparing the [3-$^{13}$C]acetoacetate or the composition described herein, wherein the method comprises the steps of:

(a) chemically synthesizing [3-$^{13}$C]acetoacetate or a composition comprising [3-$^{13}$C]acetoacetate; and (b) hyperpolarizing said [3-$^{13}$C]acetoacetate or said composition.

In various embodiments, the [3-$^{13}$C]acetoacetate is prepared from [3-$^{13}$C]ethyl acetoacetate.

In various embodiments, the chemical synthesis of [3-$^{13}$C]acetoacetate involves the saponification of [3-$^{13}$C] ethyl acetoacetate.

In various embodiments, the chemical synthesis of [3-$^{13}$C]acetoacetate comprises reacting [3-$^{13}$C]ethyl acetoacetate and a base, preferably an alkali hydroxide, more preferably lithium hydroxide, under conditions allowing said reaction.

In various embodiments, the synthesized [3-$^{13}$C]acetoacetate is hyperpolarized using Dynamic Nuclear Polarization (DNP).

In a fourth aspect, the invention provides a method of determining the spatial and temporal distribution and metabolism of [3-$^{13}$C]acetoacetate and/or its metabolites in a cell or subject, wherein the method comprises the steps of:

(a) administering the [3-$^{13}$C]acetoacetate or the composition described herein to the cell or subject; and (b) determining the distribution and metabolism of hyperpolarized [3-$^{13}$C]acetoacetate and/or its metabolites in the cell or subject by magnetic resonance imaging (MRI), magnetic resonance spectroscopy (MRS), and/or magnetic resonance spectroscopic imaging (MRSI).

In various embodiments, the cell or subject is a cell culture, an ex vivo tissue, a human, or an animal.

In various embodiments, the metabolites of [3-$^{13}$C]acetoacetate are selected from the group consisting of [5-$^{13}$C] glutamate, [1-$^{13}$C]citrate, [1-$^{13}$C]acetylcarnitine, and [3-$^{13}$C]beta-hydroxybutyrate.

In various embodiments, the magnetic resonance signals from hyperpolarized [3-$^{13}$C]acetoacetate and its metabolites are used to study the in vivo metabolism of acetoacetate and/or other ketone bodies. The term "ketone bodies" as used herein refers to three molecules, acetoacetate, 3-hydroxybutyrate, and acetone.

In various embodiments, the magnetic resonance signals from hyperpolarized [3-$^{13}$C]acetoacetate and its metabolites are used to quantify specific physiological functions of the cell or subject in healthy (e.g. starvation) and/or diseased conditions.

In various embodiments, the magnetic resonance signals from hyperpolarized [3-$^{13}$C]acetoacetate and its metabolites are used to diagnose a condition, disease, or disorder associated with the metabolism of acetoacetate and/or other ketone bodies.

In various embodiments, the condition, disease, or disorder is a cancer, diabetes, cardiovascular disease, or neurodegenerative disease.

In a fifth aspect, the invention provides a method of diagnosing a condition, disease, or disorder associated with the metabolism of acetoacetate and/or other ketone bodies in a subject, said method comprising analyzing the magnetic resonance signals obtainable by the method of the fourth aspect of the invention.

In various embodiments, the condition, disease, or disorder is a cancer, diabetes, cardiovascular disease, or neurodegenerative disease.

In a sixth aspect, the invention provides use of the [3-$^{13}$C]acetoacetate or the composition described herein in MRI, MRS, and/or MRSI.

In a seventh aspect, the invention provides use of the [3-$^{13}$C]acetoacetate or the composition described herein in the diagnosis of a condition, disease, or disorder associated with the metabolism of acetoacetate and/or other ketone bodies.

BRIEF DESCRIPTION OF THE DRAWINGS

The invention will be better understood with reference to the detailed description when considered in conjunction with the non-limiting examples and the accompanying drawings.

DETAILED DESCRIPTION OF THE INVENTION

Figure 1:
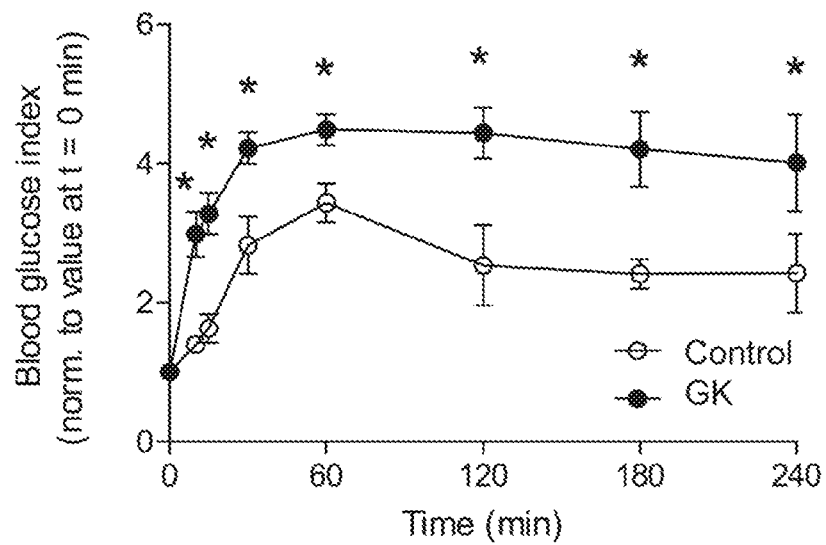
FIG. 1 shows the diabetic characteristics of GK rats. The change in blood glucose levels within 4-6 hour duration upon (A) intraperitoneal injection of oral glucose (IpGTT) and (B) upon intraperitoneal injection of insulin (IpITT). Data are means±SD (controls n=3, GK rats n=3). *P<0.05 vs. controls.
Figure 1:
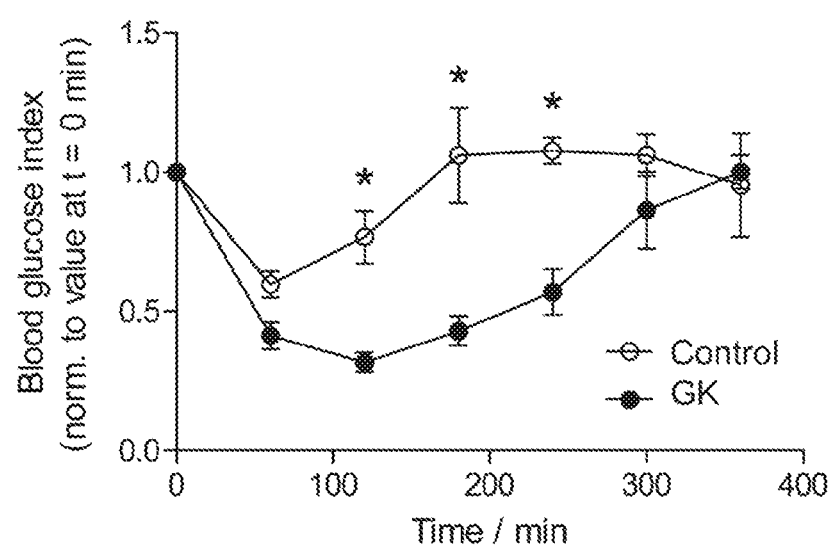

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

In a first aspect, the invention provides [3-$^{13}$C]acetoacetate, wherein at least 0.1%, 0.2%, 0.3%, 0.4%, 0.5%, 0.6%, 0.7%, 0.8% or 0.9%, more preferably at least 1%, 2%, 3%, 4%, 5%, 6%, 7%, 8% or 9%, most preferably at least 10%, 20%, 30%, 40%, 50%, 60%, 70%, 80% or 90% of said [3-$^{13}$C]acetoacetate is hyperpolarized.

The term "[3-$^{13}$C]acetoacetate" as used herein refers to any salt, preferably any pharmaceutically acceptable salt (e.g. sodium, potassium, or lithium), of [3-$^{13}$C]acetoacetic acid.

The terms "hyperpolarized" and "polarized" are used interchangeably herein for polarization of the $^{13}$C-nuclei and denote a nuclear polarization level in excess of 0.1%, in some embodiments in excess of 1% and in some embodiments in excess of 10%. Upon enhancing the nuclear polarization of the $^{13}$C-nuclei, the population difference between excited and ground nuclear spin states of these nuclei are significantly increased and thereby the MR signal intensity is amplified by a factor of hundred and more. When using a hyperpolarized $^{13}$C-enriched high T1 agent in $^{13}$C magnetic resonance spectroscopy or spectroscopic imaging, there will be essentially no interference from background signals as the natural abundance of $^{13}$C is negligible and thus the signal-to-noise ratio will be advantageously high.

The level of polarization may for instance be determined by hyperpolarized $^{13}$C-NMR, e.g. by solid-state $^{13}$C-NMR measurements in solid hyperpolarized [3-$^{13}$C]acetoacetate, e.g. solid hyperpolarized [3-$^{13}$C]acetoacetate obtained by dynamic nuclear polarization (DNP) of [3-$^{13}$C]acetoacetate. The solid-state $^{13}$C-NMR measurement according to various embodiments consists of a simple pulse-acquire NMR sequence using a low flip angle pulse. The signal intensity of the hyperpolarized [3-$^{13}$C]acetoacetate in the NMR spectrum is compared with signal intensity of [3-$^{13}$C]acetoacetate in a NMR spectrum acquired before the polarization process. The level of polarization is then calculated from the ratio of the signal intensities before and after polarization.

In a similar way, the level of polarization for dissolved hyperpolarized [3-$^{13}$C]acetoacetate may be determined by liquid state NMR measurements. Again the signal intensity of the dissolved hyperpolarized [3-$^{13}$C]acetoacetate is compared with the signal intensity of the dissolved [3-$^{13}$C] acetoacetate before polarization or after the polarization has decayed. The level of polarization is then calculated from the ratio of the signal intensities of [3-$^{13}$C]acetoacetate before and after polarization.

The [3-$^{13}$C]acetoacetate described herein can be in any form, e.g. as a solid or in solution, and can be prepared by the method detailed below in the third aspect of the invention.

In a second aspect, the invention provides a composition comprising the [3-$^{13}$C]acetoacetate described herein.

As will be described below, the composition according to the present invention may be used as an imaging medium for $^{13}$C magnetic resonance imaging (MRI), magnetic resonance spectroscopy (MRS), and/or magnetic resonance spectroscopic imaging (MRSI) in living human or non-human animal beings. For this purpose, the composition is provided as a composition that is suitable for being administered to a living human or non-human animal body. Such a composition in various embodiments comprises in addition to [3-$^{13}$C]acetoacetate, an aqueous carrier, in various embodiments a physiologically tolerable and pharmaceutically accepted aqueous carrier like water, a buffer solution or saline. Such an imaging medium may further comprise conventional pharmaceutical or veterinary carriers or excipients, e.g. formulation aids such as are conventional for diagnostic compositions in human or veterinary medicine.

Further, the composition according to the present invention may be used as an imaging medium for in vitro $^{13}$C-based applications, i.e. in cell cultures, body samples such as blood samples, ex vivo tissues such as biopsy tissue or isolated organs. For this purpose, the composition is provided as being suitable for being added to, for instance, cell cultures, blood samples, ex vivo tissues like biopsy tissue or isolated organs. Such a composition in various embodiments comprises in addition to [3-$^{13}$C]acetoacetate a solvent which is compatible with and used for in vitro cell or tissue assays, for instance DMSO or methanol or solvent mixtures comprising an aqueous carrier and a non-aqueous solvent, for instance mixtures of DMSO and water or a buffer solution or methanol and water or a buffer solution. As it is apparent for a skilled person, pharmaceutically acceptable carriers, excipients and formulation aids may be present in such a composition but are not required for such a purpose.

In a third aspect, the invention provides a method of preparing hyperpolarized [3-$^{13}$C]acetoacetate or a composition comprising hyperpolarized [3-$^{13}$C]acetoacetate, wherein the method comprises the steps of (a) chemically synthesizing [3-$^{13}$C]acetoacetate or a composition comprising [3-$^{13}$C]acetoacetate; and (b) hyperpolarizing said [3-$^{13}$C]acetoacetate or said composition.

In various embodiments, [3-$^{13}$C]acetoacetate may be prepared from [3-$^{13}$C]ethyl acetoacetate. In the preparation [3-$^{13}$C]ethyl acetoacetate could be used as a starting material as this is a commercially available compound.

In various embodiments, the chemical synthesis of [3-$^{13}$C]acetoacetate involves the saponification of [3-$^{13}$C] ethyl-acetoacetate.

In various embodiments, the chemical synthesis of [3-$^{13}$C]acetoacetate comprises reacting [3-$^{13}$C]ethyl acetoacetate and a base, preferably an alkali hydroxide, more preferably lithium hydroxide, under conditions allowing said reaction.

The following is a preferred protocol for synthesizing [3-$^{13}$C]acetoacetate according to a non-limiting embodiment: placing 1 gram of [3-$^{13}$C]ethyl acetoacetate (Cambridge Isotope Laboratories, Massachusetts, USA), 4.8 mL of water, and 1.9 mL of 4 mol/L lithium hydroxide (Sigma Aldrich, Missouri, USA) in a water bath at 40° C. for 4 hours; evaporating the pale yellow solution to dryness; extracting lithium [3-$^{13}$C]acetoacetate at room temperature by adding three successive 3 mL portions of absolute methanol; removing insoluble material by centrifugation and adding absolute ether slowly to the clear methanol solution until the commencement of crystallization; after standing for 30 min, adding 5 volume of ether slowly and chilling the mixture at 4° C.; collecting the crystals by suction filtration, drying the collected crystals in vacuum after washing with chilled ether; recrystallizing the product twice by dissolving in 6 mL of absolute methanol per gram; and removing insoluble material by centrifugation, and adding absolute ether. After two recrystallizations, the yield of about 70% may be expected. The purity of the [3-$^{13}$C] acetoacetate synthesized following the above protocol can be assessed by hyperpolarized $^{13}$C-NMR. Within the chemical shift region of 171-183 ppm, the hyperpolarized signals of natural abundance [1-$^{13}$C]acetoacetate at 174.6 ppm and an impurity at 181.0 ppm can be observed.

One skilled in the art would readily appreciate that the protocols described in the present application and the numbers disclosed therein are for explanatory purposes only, and are not intended in any way to limit the invention.

The synthesized [3-$^{13}$C]acetoacetate may be further hyperpolarized using any techniques available in the art. Such techniques include, without limitation, and Dynamic Nuclear Polarization (DNP), a solid-state polarization technique using unpaired electrons to reach a spin order of unity within hours.

Hyperpolarization of NMR active $^{13}$C-nuclei may be achieved by different methods available in the art. Preferred methods are polarization transfer from a noble gas, "brute force", spin refrigeration, Parahydrogen and Synthesis Allows Dramatically Enhanced Nuclear Alignment (PASADENA), and DNP.

One way for obtaining hyperpolarized [3-$^{13}$C]acetoacetate is by polarization transfer from a hyperpolarized noble gas. Noble gases having non-zero nuclear spin can be hyperpolarized by the use of circularly polarized light. A hyperpolarized noble gas, in various embodiments He or Xe, or a mixture of such gases, may be used to effect hyperpolarization of $^{13}$C-nuclei. The hyperpolarized gas may be in the gas phase, it may be dissolved in a liquid/solvent, or the hyperpolarized gas itself may serve as a solvent. Alternatively, the gas may be condensed onto a cooled solid surface and used in this form, or allowed to sublime. In various embodiments, there is an intimate mixing of the hyperpolarized gas with [3-$^{13}$C]acetoacetate.

Another way for obtaining hyperpolarized [3-$^{13}$C]acetoacetate is that polarization is imparted to $^{13}$C-nuclei by thermodynamic equilibration at a very low temperature and high field. Hyperpolarization compared to the operating field and temperature of the NMR spectrometer is effected by use of a very high field and very low temperature ("brute force"). The magnetic field strength used should be as high as possible, preferably at least 1 T or 5 T, more preferably at least 15 T, most preferably at least 20 T. The temperature should be very low, e.g. 4.2 K or less, preferably 1.5 K or less, more preferably 1.0 K or less, and most preferably 100 mK or less.

Another way for obtaining hyperpolarized [3-$^{13}$C]acetoacetate is the spin refrigeration method. This method covers spin polarization of a solid compound or system by spin refrigeration polarization. The system is doped with or intimately mixed with suitable crystalline paramagnetic materials such as $Ni^{2+}$, lanthanide or actinide ions with a symmetry axis of order three or more. The instrumentation is simpler than required for DNP with no need for a uniform magnetic field since no resonance excitation field is applied. The process is carried out by physically rotating the sample around an axis perpendicular to the direction of the magnetic field. The pre-requisite for this method is that the paramagnetic species has a highly anisotropic g-factor. As a result of the sample rotation, the electron paramagnetic resonance will be brought into contact with the nuclear spins, leading to a decrease in the nuclear spin temperature. Sample rotation is carried out until the nuclear spin polarization has reached a new equilibrium.

In the preferred embodiment, DNP (dynamic nuclear polarization) is used to obtain hyperpolarized [3-$^{13}$C]acetoacetate. Dynamic nuclear polarization (DNP) is a technique that allows the low sensitivity of magnetic resonance spectroscopy to be overcome by inducing high nuclear polarization of $^{13}C$ substrates at low temperatures in the solid state. Using a rapid dissolution process, this high polarization can be briefly maintained in the liquid state at room temperature. Since this eliminates the necessity of glass formers and/or high amounts of solvent(s) in the sample, a highly concentrated sample can be prepared and used in the DNP process. In DNP, polarization of MR active nuclei in a compound to be polarized is effected by a polarization agent or so-called DNP agent, a compound comprising unpaired electrons. During the DNP process, energy, normally in the form of microwave radiation, is provided, which will initially excite the DNP agent. Upon decay to the ground state, there is a transfer of polarization from the unpaired electron of the DNP agent to the NMR active nuclei of the compound to be polarized, e.g. to the $^{13}C$ nuclei in [3-$^{13}C$]acetoacetate. Generally, a moderate or high magnetic field and a very low temperature are used in the DNP process, e.g. by carrying out the DNP process in liquid helium under vacuum and a magnetic field of about 1 T or above. Alternatively, a moderate magnetic field and any temperature at which sufficient polarization enhancement is achieved may be employed.

To polarize a compound by the DNP method, a composition comprising the compound to be polarized and a DNP agent is prepared which is then frozen and inserted into a DNP polarizer for polarization. After the polarization, the frozen solid hyperpolarized composition is rapidly transferred into the liquid state, either by melting it or by dissolving it in a suitable dissolution medium. According to an embodiment, there is dissolution, wherein the dissolution process of a frozen hyperpolarized composition and suitable devices therefore as well as the melting process and suitable devices for the melting are known in the art.

The following is a preferred protocol for hyperpolarization employing DNP according to a non-limiting embodiment: mixing 50 mg of [3-$^{13}C$]acetoacetate with 5.5 mg of trityl-radical (OX063, GE Healthcare), 250 µl of gadoterate meglumine (1.2 mmol/L, Dotareme, Guerbet), and 93 µL of DMSO (25% v/v) to achieve a solution comprising 1.23 mol/L of [3-$^{13}C$]acetoacetate, 9.3 mmol/L of OX063, and 0.80 mmol/L of gadolinium; and hyperpolarizing 200 µL of the sample in a polarizer (Hypersense, Oxford Instruments, Oxford, UK), with 120 min of microwave irradiation at 94.097 GHz. The hyperpolarized sample may be subsequently dissolved in 3 mL of pressurized and heated Tris-EDTA buffer with pH 7.80, to yield a solution of 80 mmol/L hyperpolarized [3-$^{13}C$]acetoacetate with a polarization of 10% and physiological temperature and pH.

In a fourth aspect, the invention provides a method of determining the spatial and temporal distribution and metabolism of hyperpolarized [3-$^{13}C$]acetoacetate and/or its metabolites in a cell or subject, wherein the method comprises the steps of (a) administering the [3-$^{13}C$]acetoacetate or the composition described herein to the cell or subject; and (b) determining the distribution and metabolism of hyperpolarized [3-$^{13}C$]acetoacetate and/or its metabolites in the cell or subject by magnetic resonance imaging (MRI), magnetic resonance spectroscopy (MRS), and/or magnetic resonance spectroscopic imaging (MRSI).

The cell or subject may be, without limitation, a cell culture, an ex vivo tissue, a human or an animal.

The metabolites of [3-$^{13}C$]acetoacetate include, but are not limited to, [5-$^{13}C$]glutamate, [1-$^{13}C$]citrate, [1-$^{13}C$]acetylcarnitine and [3-$^{13}C$]beta-hydroxybutyrate.

It should be understood that the signal of the hyperpolarized [3-$^{13}C$]acetoacetate decays over time due to relaxation and metabolism. Hence the T1 value of [3-$^{13}C$]acetoacetate must be sufficiently high to enable the agent to be distributed to the target site in the patient's body in a highly hyperpolarized state. The inventors of the present application have surprisingly found that the hyperpolarized [3-$^{13}C$]acetoacetate described herein can be used to determining the spatial and temporal distribution of hyperpolarized [3-$^{13}C$]acetoacetate and its metabolites in a cell or subject.

Using the presently described method, magnetic resonance signals from hyperpolarized [3-$^{13}C$]acetoacetate and its metabolites can be detected, and images, metabolic data, kinetics data of one or more enzymes (e.g. 3-OHB, BDH-1, ACAT, CAT, CS, and/or GDH), transport kinetic data, diffusion data, relaxation data, and/or physiological data can be generated from said detected signals. Such data can be used to study the in vivo metabolism of acetoacetate and/or other ketone bodies.

Further, exploring $^{13}C$ fluxes through acetoacetate-related metabolic pathways can also enable the quantification of specific physiological functions of the cell or subject in healthy (e.g. starvation) and/or diseased conditions. It can also enable the diagnosis of conditions, diseases, or disorders associated with the metabolism of acetoacetate and/or other ketone bodies, including but without limitation cancers, diabetes, cardiovascular diseases (e.g. cardiac hypertrophy), and neurodegenerative diseases in human or non-human subjects.

In various embodiments, the method of the present invention is carried out in vivo and the information obtained is used in assessing the efficacy of potential drugs that alter the metabolism of acetoacetate and/or other ketone bodies in vivo. In these embodiments, the method of the present invention may be carried out in, for instance, test animals or in volunteers in a clinical trial. To the test animal or volunteer a potential drug is administered and the metabolism of acetoacetate and/or other ketone bodies is determined by $^{13}C$-MR detection according to the method of the present invention. Information about the efficacy of the potential drug may be obtained by determining the variation of the metabolism of acetoacetate and/or other ketone bodies before and after treatment, e.g. over a certain period with repeated treatment. Such a drug efficacy assessment may be carried out in pre-clinical research (test animals) or in clinical trials.

In various embodiments, the method of the present invention is carried out in vivo or in vitro and the information obtained is used to assess response to treatment and/or to determine treatment efficacy in diseased patients undergoing treatment for their disease associated with the metabolism of acetoacetate and/or other ketone bodies.

As stated earlier the information obtained by the method of the present invention may be used in a subsequent step for various purposes. Another purpose may be to gain insight into disease states that are associated with the metabolism of acetoacetate and/or other ketone bodies, i.e. identifying patients at risk, early detection of diseases, evaluating disease progression, severity and complications related to a disease.

In various embodiments, the method of the present invention is carried out in vivo or in vitro and the information obtained is used to monitor progression of a disease. This may be useful for diseases or disorders where the disease has not progressed to a level where treatment is indicated or recommended, e.g. because of severe side effects associated with said treatment. In such a situation the choice of action is "watchful waiting", i.e. the patient is closely monitored for disease progression and early detection of deterioration. In this embodiment, the method of the present invention may be used to determine the metabolism of acetoacetate and/or other ketone bodies and to make subsequent determinations over a period at a certain frequency. It can be expected that a change in the metabolism of acetoacetate and/or other ketone bodies may indicate progress and worsening of a disease and the said decrease can be used by the physician to decide on commencement of treatment. To carry out the method of the present invention for the above-mentioned purpose in vitro requires that suitable samples from a patient under treatment are obtainable, e.g. tissue samples or body samples like blood samples.

In various embodiments, the method according to the present invention is used for in vivo MR tumour imaging, tumour therapy monitoring and/or tumour staging.

In various embodiments, the method of the present invention is carried out in vivo or in vitro and the information obtained is used for determining the severity of a disease. Often diseases progress from their onset over time. Depending on the kind of symptoms and/or the finding of certain clinical markers diseases are characterized by certain stages, e.g. an early (mild) stage, a middle (moderate) stage and a severe (late) stage. More refined stages are common for certain diseases. A variety of clinical markers is known to be used for staging a disease including more specific ones like certain enzymes or protein expression but also more general ones like blood values, electrolyte levels etc. In this context, a change in the metabolism of acetoacetate and/or other ketone bodies may be such a clinical marker that can be used, alone or in combination with other markers and/or symptoms, to determine a disease stage and thus severity of a disease. Hence, it may be possible to use the method of the present invention for determining the metabolism of acetoacetate and/or other ketone bodies in a patient in a quantitative way and from the metabolism of acetoacetate and/or other ketone bodies obtained staging the patient's disease. The metabolism of acetoacetate and/or other ketone bodies which are characteristic for a certain disease stage may be established by determining the metabolism of acetoacetate and/or other ketone bodies according to the method of the present invention in patients having for instance a disease in an early, middle and late stage and defining a range of metabolism profiles of acetoacetate and/or other ketone bodies which is characteristic for a certain stage.

In various embodiments, the method of the present invention is carried out in vivo or in vitro and the information obtained is used for identifying and assessing complications related to a disease. With the method of the present invention, the metabolism of acetoacetate and/or other ketone bodies may be determined in an organ-specific way, for instance by in vivo $^{13}$C-MR detection carried out with surface coils placed over the heart or the kidney.

Anatomical and/or, where suitable, perfusion information may be included in the method of the present invention when carried out in vivo. Anatomical information may for instance be obtained by acquiring a proton or $^{13}$C-MR image with or without employing a suitable contrast agent before or after the method of the present invention.

As described above, also encompassed in the present invention is a method of diagnosing a condition, disease, or disorder associated with the metabolism of acetoacetate and/or other ketone bodies in a subject, said method comprising analyzing the magnetic resonance signals obtainable by the method of the fourth aspect of the present application, wherein the condition, disease, or disorder is preferably a cancer, diabetes, cardiovascular disease, or neurodegenerative disease.

For example, [5-$^{13}$C]glutamate alone or in combination with [1-$^{13}$C]citrate can be used to diagnose diabetes, and increased ketone body utilization can be a good biomarker for cardiac hypertrophy and reduced ejection fraction in diabetic subjects.

It should be noted that at least one step in this method is not directly performed on a human or animal body.

Uses of the [3-$^{13}$C]acetoacetate or the composition described herein in MRI, MRS, and/or MRSI, or in the diagnosis of a condition, disease, or disorder associated with the metabolism of acetoacetate and/or other ketone bodies are also within the scope of the present invention.

The present invention is further illustrated by the following examples. However, it should be understood, that the invention is not limited to the exemplified embodiments.

EXAMPLES

Materials and Methods
Animals
Male non-obese diabetic Goto-Kakizaki (GK/MolTac; n=10) rats bred by Taconic (New York, US) were ordered from InVivos (Singapore). Male wild-type Wistar Han rats (n=10) were purchased from InVivos (Singapore) and served as controls. At 24 weeks of age, the animals underwent $^{13}$C MRS and MRI to determine myocardial ketone body utilization and cardiac function. The animals were anaesthetized with isoflurane (3% for induction; 1.5-2% for maintenance) in medical air and oxygen at a flow rate of 2.0 L/min and 0.5 L/min, respectively. A catheter was inserted into the tail vein for intravenous administration of the hyperpolarized [3-$^{13}$C] acetoacetate inside the MRI scanner. At the end of the study, the animals were sacrificed. Blood and organs were collected and stored at −80° C. for biochemical analysis. All procedures involving animals were approved by A*STAR Institutional Animal Care and Use Committee (#171204)

[3-$^{13}$C]Acetoacetate Synthesis, Polarization and Dissolution
Chemical Synthesis—
The chemical synthesis of [3-$^{13}$C]acetoacetate involves the saponification of [3-$^{13}$C]ethyl-acetoacetate which was performed according to Hall et al (Aubert, et al. Circulation. 2016; 133:698-705). More specifically, the following protocol was followed: placing 1 gram of [3-$^{13}$C]ethyl acetoacetate (Cambridge Isotope Laboratories, Massachusetts, USA), 4.8 mL of water, and 1.9 mL of 4 mol/L lithium hydroxide (Sigma Aldrich, Missouri, USA) in a water bath at 40° C. for 4 hours; evaporating the pale yellow solution to dryness; extracting lithium [3-$^{13}$C]acetoacetate at room temperature by adding three successive 3 mL portions of absolute methanol; removing insoluble material by centrifugation and adding absolute ether slowly to the clear methanol solution until the commencement of crystallization; after standing for 30 min, adding 5 volume of ether slowly and chilling the mixture at 4° C.; collecting the crystals by suction filtration, drying the collected crystals in vacuum after washing with chilled ether; recrystallizing the product twice by dissolving in 6 mL of absolute methanol per gram; and removing insoluble material by centrifugation, and adding absolute ether. After two recrystallizations, the yield of about 70% may be expected. The purity of the [3-$^{13}$C] acetoacetate synthesized following the above protocol can be assessed by hyperpolarized $^{13}$C-NMR. Within the chemical shift region of 171-183 ppm, the hyperpolarized signals of natural abundance [1-$^{13}$C]acetoacetate at 174.6 ppm and an impurity at 181.0 ppm can be observed.

Polarization and Dissolution—

Approximately 51 mg of [3-$^{13}$C]acetoacetate, doped with 5.5 mg of trityl-radical (OX063, GE Healthcare), 250 µl of gadoterate meglumine (1.2 mmol/L, Dotarem®, Guerbet) and 93 mL of DMSO (25% v/v) was prepared. Total volume is approximately 370 mL, resulting in 1.23 mol/L of [3-$^{13}$C] acetoacetate, 9.3 mmol/L of OX063, and 0.80 mmol/L of gadolinium. 200 mL of the sample was hyperpolarized in a polarizer (Hypersense, Oxford Instruments, Oxford, UK), with 120 min of microwave irradiation at 94.097 GHz. The polarized sample was subsequently dissolved in 3 mL of pressurized and heated Tris-EDTA buffer with pH 7.80, to yield a solution of 80 mmol/L hyperpolarized [3-$^{13}$C]acetoacetate with a polarization of 10% and physiological temperature and pH.

Ketone Body Utilization in the Heart In Vivo Measured by Hyperpolarized $^{13}$C-MRS Rats were positioned supine in a 9.4 T horizontal bore MR scanner interfaced to a Avance III HD console (Biospec, Bruker, Germany), with the heart directly above a dual-tuned ($^{1}$H/$^{13}$C) rat surface coil (diameter: 30 mm). Correct positioning was confirmed by the acquisition of an axial proton FLASH image (TE/TR, 8.0/100.0 ms; matrix size, 128×128; FOY, 40×40 mm; slice thickness, 1.5 mm; excitation flip angle, 30°). A cardiac-triggered and respiratory-gated shim was used to reduce the proton linewidth to approximately 160 Hz. Immediately before injection, a respiratory-gated $^{13}$C MR pulse-acquire spectroscopy sequence was initiated. Then, hyperpolarized [3-$^{13}$C]acetoacetate (0.75-1.05 mL; 0.240 mmol/kg body weight) was injected via tail vein at a rate of 6 mL/min. Sixty individual heart spectra were acquired over 2 minutes after injection (TR, 2 s; excitation flip angle, 25°; sweep width, 8,000 Hz; acquired points, 4,096; frequency centered at 190 ppm from tetramethylsilane (TMS) standard).

$^{13}$C-MRS Data Analysis

Cardiac $^{13}$C MR spectra were analyzed using the AMA-RES algorithm as implemented in the jMRUI software package (Naressi A, et al. Magn Reson Mater Physics, Biol Med. 2001; 12:141). Spectra were baseline and DC offset-corrected based on the last half of acquired points. To quantify myocardial ketone metabolism, spectra were summed over the first 30 seconds upon acetoacetate arrival. Peaks corresponding to [3-$^{13}$C]acetoacetate and its metabolic derivatives [5-$^{13}$C]glutamate, [1-$^{13}$C]acetoacetate, and [1-$^{13}$C]acetylcarnitine were fitted with prior knowledge assuming a Lorentzian line shape, peak frequencies, relative phases, and linewidths. The fitted amplitudes were then normalized to the amplitude of [3-$^{13}$C]acetoacetate.

In Vivo Assessment of Cardiac Function

Cardiac MRI measurements were performed at a 9.4 T preclinical MRI system (Biospec, Bruker, Germany), in the same session as the $^{13}$C MRS. Cardiac-triggered respiratory-gated cine-MRI was acquired in five to seven contiguous short-axis slices (slice thickness: 1.5 mm) covering the entire heart. The imaging parameters were FOY 40×40 mm2, matrix size 128×128, TE/TR 1.23/8.0 millisecond, 15° SLR excitation pulse, NAE 5, number of frames: 23-27 per cardiac cycle.

Cine-MRI images were exported into DICOM format and loaded into ImageJ (NIH, Maryland, USA) for subsequent region-of-interest analysis. For LV volumes and mass measurements, end-diastolic and end-systolic frames were selected according to maximal and minimal ventricular volume. In both frames, the epicardial and LV cavity border were outlined manually. The difference in area between these two ROIs multiplied by the slice thickness of 1.5 mm yielded the myocardial volume. L V mass was obtained by multiplying the myocardial volume with the specific gravity of 1.05 g/cm$^3$ (Manning, et al. *Am J Physiol—Hear Circ Physiol.* 1994; 266:HI672 LP-HI675). The end-systolic (ESV) and end-diastolic (EDV) volumes are calculated as the LV cavity area multiplied by the slice thickness. Based on ESV and EDV volumes, all parameters characterizing cardiac function, such as stroke volume (SV=EDV−ESV), ejection fraction (EF=SV/EDV), and cardiac output (CO=SV×heart rate) were calculated accordingly (Schneider, et al. *J Magn Reson Imaging.* 2003; 18:691-701.)

Determination of Blood Parameters

Blood samples (4 µL) were collected from the tail at fed condition (immediately prior to MR measurements) and after 16.5 hours of fasting, to determine blood glucose, triglycerides, and ketone body levels. Intraperitoneal glucose tolerance test (IpGTT) and insulin tolerance test (Ip-ITT) were determined. Serum insulin, glucagon, and acetoacetate levels were determined in blood samples collected at sacrifice. Blood samples were collected in micro-collection tubes (BD, New Jersey, USA) with serum separator additive and left to clot for 30 min at room temperature. Thereafter, serum was collected after centrifugation at 15,000 g for 2 min. Serum insulin and glucagon levels were determined using ultrasensitive mouse insulin ELISA and glucagon ELISA kits, respectively (Mercodia, Uppsala, Sweden). Serum acetoacetate levels were determined using acetoacetate colorimetric assay kit (BioVision, Inc., San Francisco, US).

Intraperitoneal Glucose Tolerance Test (IpGTT)

The glucose tolerance was determined by measuring the blood glucose levels before and at 5, 10, 15, 30, 60, 120, 180, and 240 minutes after intraperitoneal injection of glucose solution (1 g/kg body weight). The animals were fasted for 16.5 hours prior to the experiments.

Intraperitoneal Insulin Tolerance Test (IpITT)

The response to insulin glucose tolerance was determined by measuring the blood glucose levels before and at 60, 120, 180, 240, 300, and 360 minutes after intraperitoneal injection of insulin solution (1 U/kg body weight).

Determination of SCOT Activity

The assay to determine SCOT activity was performed as described previously (Tanaka, et al. *Int J Andra.* 2003; 26:52-56). Briefly, 2.0 mL of solution comprising 50 mmol/L Tris-HCl buffer (pH 8.5), 0.2 mmol/L succinyl-CoA, 5 mmol/L lithium acetoacetate, 5 mmol/L MgCl2 and 5 mmol/L iodoacetamide (to inhibit acetoacetyl-CoA thiolase) was contained in a silica cuvette (1 cm). 0.4 mg of supernatant from the homogenized tissue was added and the rate of increase in absorption at 313 nm was measured for 2 min. Under this assay condition, a solution containing 1 mmol/L of accetoacetyl-CoA has an absorbance of 18.4 at 313 nm. Protein concentrations were determined using bovine serum albumin as the standard.

Statistical Analysis

All statistical analysis was performed with the Graphpad Prism software package. The data were presented as means±SD. Statistical significance in hyperpolarized $^{13}$C metabolite signal ratios and ex-vivo cardiac enzyme activity comparisons were assessed by using a two-tailed unpaired Student's t-test. Correlations between parameters were assessed using a Pearson's correlation. Statistical significance in the IpGTT curve was determined using the Holm-Sidak method. The significance was set at P<0.05.

Example 1: Characterization of Used Animals

At 24 weeks old, body weight was lower in the diabetic rats than in control rats (Table 1). The diabetic rats showed higher blood glucose and TG levels than controls (P<0.0001 and P=0.049, respectively), while insulin levels were lower in the diabetic rats compared with control rats (P=0.001; Table 1). The diabetic rats had impaired glucose tolerance (FIG. 1A), while administration of insulin lowered blood glucose during insulin tolerance test (FIG. 1B).

TABLE 1

Blood parameter at 24 weeks.

|  | Control | Diabetic | P value |
|---|---|---|---|
| Body weight | 479.8 ± 30.0 | 403.3 ± 16.5*** | <0.0001 |
| Glucose (fasting) | 5.3 ± 0.5 | 9.3 ± 1.1*** | <0.0001 |
| β-OHB (fasting) | 1.1 ± 0.2 | 1.1 ± 0.3 | 0.580 |
| β-OHB (fed) | 0.3 ± 0.1 | 0.4 ± 0.1 | 0.540 |
| Acetoacetate (fed) | 0.52 ± 0.02 | 0.55 ± 0.02** | 0.002 |
| Total ketone bodies (fed) | 0.86 ± 0.11 | 0.92 ± 0.08 | 0.185 |
| TG (fasting) | 1.95 ± 0.32 | 2.49 ± 0.74* | 0.049 |
| Insulin (fed) | 9.3 ± 3.7 | 3.2 ± 1.6** | 0.001 |
| Glucagon (fed) | 54.9 ± 29.8 | 57.1 ± 25.5 | 0.867 |

β-OHB: β-hydroxybutyrate;
TG: triglycerides;
total ketone bodies: β-OHB + acetoacetate.
Data are means ± SD (control N = 10 and diabetic rats N = 9.
*P < 0.05,
**P < 0.01,
***P < 0.001.

Figure 2:
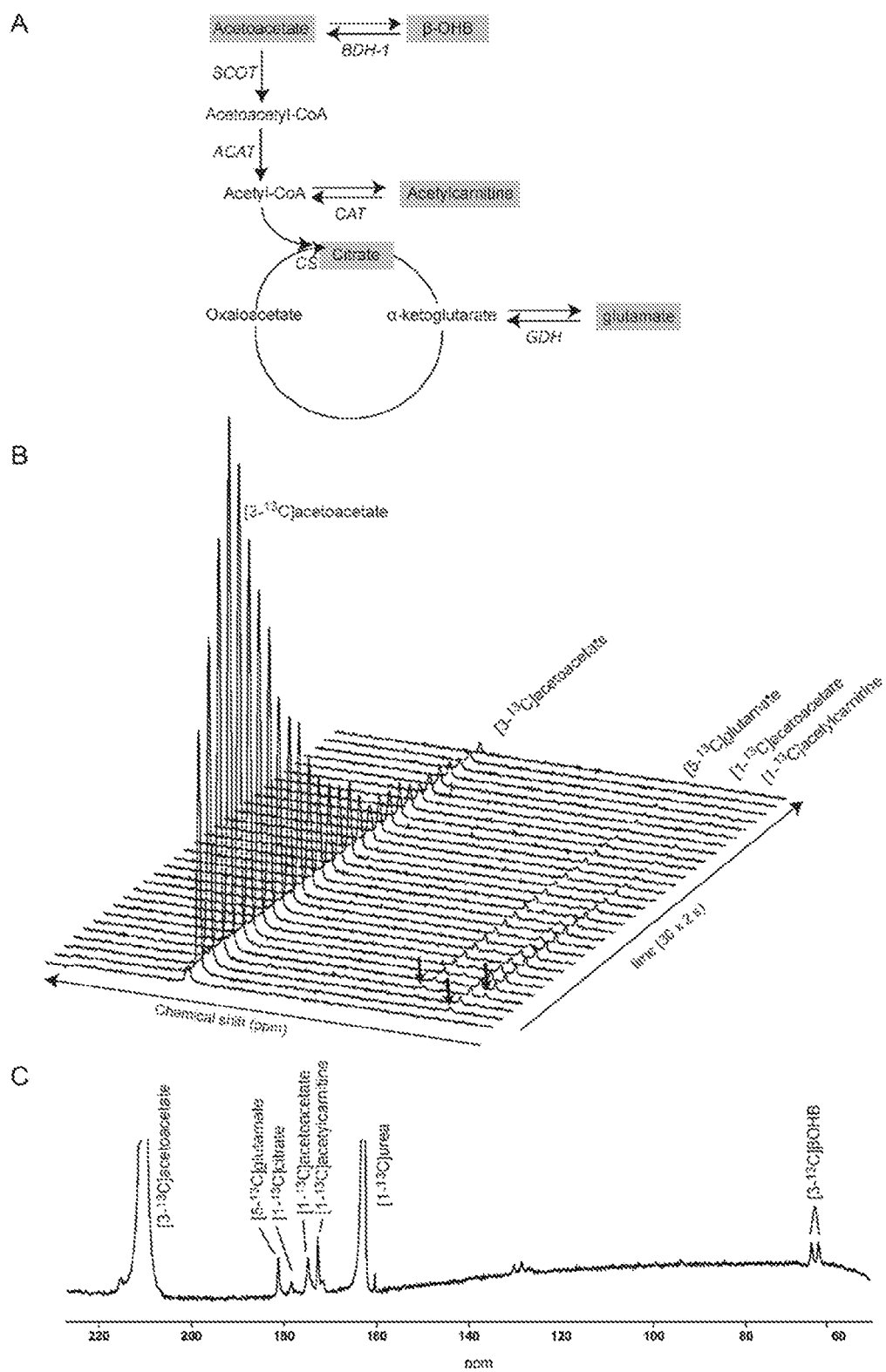
FIG. 2 shows the detection of ketone metabolic products in the heart using hyperpolarized $^{13}$C MRS. (A) Metabolic fate of hyperpolarized [3-$^{13}$C]acetoacetate. Metabolites can be detected by in vivo $^{13}$C MRS in the heart. (B) Dynamic in vivo cardiac $^{13}$C MR spectra over 1 minute period after [3-$^{13}$C]acetoacetate injection, with a time resolution of 2 s. The spectra are truncated at 170 ppm. Black arrows indicate the first detection of the corresponding peaks. (C) A representative cardiac $^{13}$C MR spectrum, summed over 40 seconds upon [1-$^{13}$C]acetoacetate arrival, with [1-$^{13}$C] urea used as an external reference. β-OHB: β-hydroxybutyrate, BDH-1: 3-hydroxybutyrate dehydrogenase-1, SCOT: succinyl-CoA:3-ketoacid-coenzyme A transferase, ACAT: acetoacetyl-CoA thiolase, CAT: carnitine-acylcarnitine translocase, CS: citrate synthase, GDH: glutamate dehydrogenase.
Figure 7:
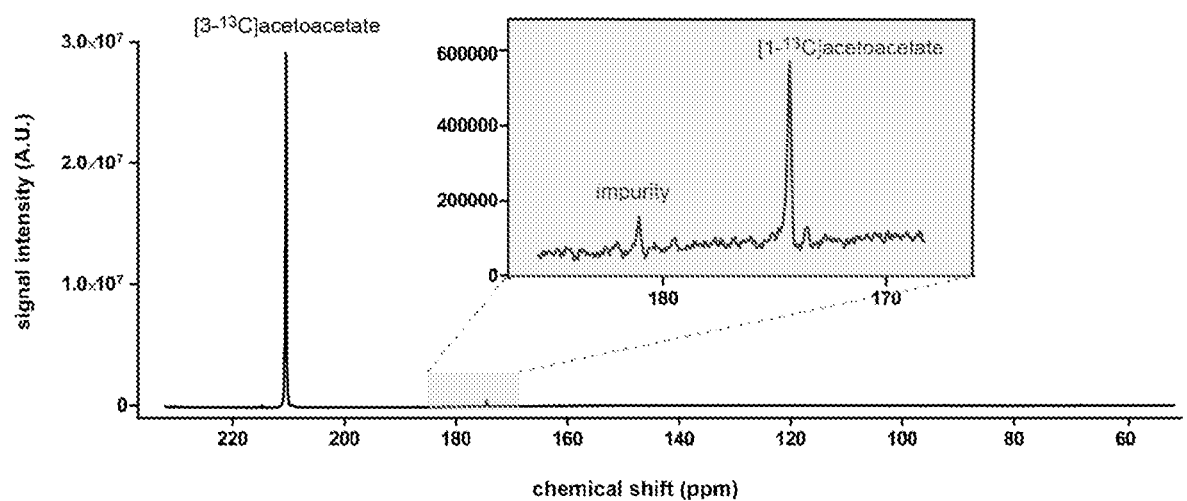
FIG. 7 shows $^{13}$C MR spectrum of 4 mM hyperpolarized [3-$^{13}$C]acetoacetate. Upon injection in vivo, 4 mM is the typical [3-$^{13}$C]acetoacetate concentration in blood. The [3-$^{13}$C]acetoacetate is seen at 209.9 ppm. The natural abundant [1-$^{13}$C]acetoacetate appears at 174.6 ppm, and an impurity peak is visible at 181.0 ppm. The impurity peak intensity is 0.19±0.01% of the [3-$^{13}$C]acetoacetate signal, which is negligible in comparison to the expected metabolite peak, i.e. [5-$^{13}$C]glutamate at 181.2 ppm, present at a concentration range of 2-4% of the [3-$^{13}$C]acetoacetate signal.

Example 2: Hyperpolarization and Lifetime of the Synthesized [3-$^{13}$C]Acetoacetate Allow Probing Ketone Body Utilization In Vivo $^{13}$C MRS The Examiner first determined whether the synthesized [3-$^{13}$C]acetoacetate can be hyperpolarized with sufficient polarization and lifetime for in vivo application. After 120 minutes of microwave irradiation at 1.2 K, the achieved polarization was 10.3±1.2% and T1 was 28.2±3.1 s. A representative hyperpolarized $^{13}$C MR spectrum of 4 mM [3-$^{13}$C]acetoacetate solution is shown in FIG. 7. Besides the main substrate peak at 209.9 ppm and the natural abundance [1-$^{13}$C]acetoacetate at 174.6 ppm, an impurity peak was detected at 181.0 ppm. The amplitude of the impurity peak is 0.19±0.01% of the [3-$^{13}$C]acetoacetate signal. The impurity peak is very close to the expected [5-$^{13}$C]glutamate peak at 181.2 ppm (FIG. 2B). However, the concentration of the impurity is negligible in comparison to the concentration range of the glutamate (2-4% of the [3-$^{13}$C]acetoacetate signal). Additionally, signal of natural abundant [1-$^{13}$C] acetoacetate at 174.6 ppm were visible in the chemical shift region of 171-183 ppm, which is the range of the downstream products of ketone metabolism (FIG. 2B).

Acetoacetate is a major entry ketone body for energy production in the heart. The oxidation of acetoacetate generates two metabolic intermediates: (1) μ-OHB, catalyzed by mitochondrial β-hydroxybutyrate dehydrogenase (BDH-1), and (2) acetoacetyl-CoA (AcAc-CoA), catalyzed by the rate-limiting SCOT. AcAc-CoA is then rapidly converted into acetyl-CoA by acetoacetyl-CoA thiolase (ACAT). This fuel unit is then either stored as acetylcarnitine upon catalysis by carnitine acetyltransferase (CAT), or incorporated into the tricarboxylic acid (TCA) cycle via citrate synthase (CS) mediation.

For in vivo applications, the inventors administered hyperpolarized [3-$^{13}$C]acetoacetate intravenously then followed the evolution of the $^{13}$C MR spectra within a two minute period, which revealed the incorporation of the $^{13}$C label from [3-$^{13}$C]acetoacetate into its metabolic products (FIG. 2A-B). The [3-$^{13}$C]acetoacetate peak at 209.9 ppm was first detected, followed by the appearance of the natural abundant [1-$^{13}$C]acetoacetate at 174.6 ppm. The $^{13}$C label incorporation from [3-$^{13}$C]acetoacetate into [1-$^{13}$C]acetylcarnitine at 172.6 ppm and [5-$^{13}$C]glutamate at 181.2 ppm appeared 2-4 seconds later, which indicate that these are downstream products from ketone body metabolism. Due to its low signal, [1-$^{13}$C]citrate at 178.4 ppm was not revealed until 8-10 seconds later.

A representative $^{13}$C MR spectrum of the summed spectra over 40 seconds upon acetoacetate arrival is shown in FIG. 2C. In addition to the above-mentioned resonances, [3-$^{13}$C] β-OHB resonances at 69.2 ppm and 67.8 ppm were also observed.

Figure 3:
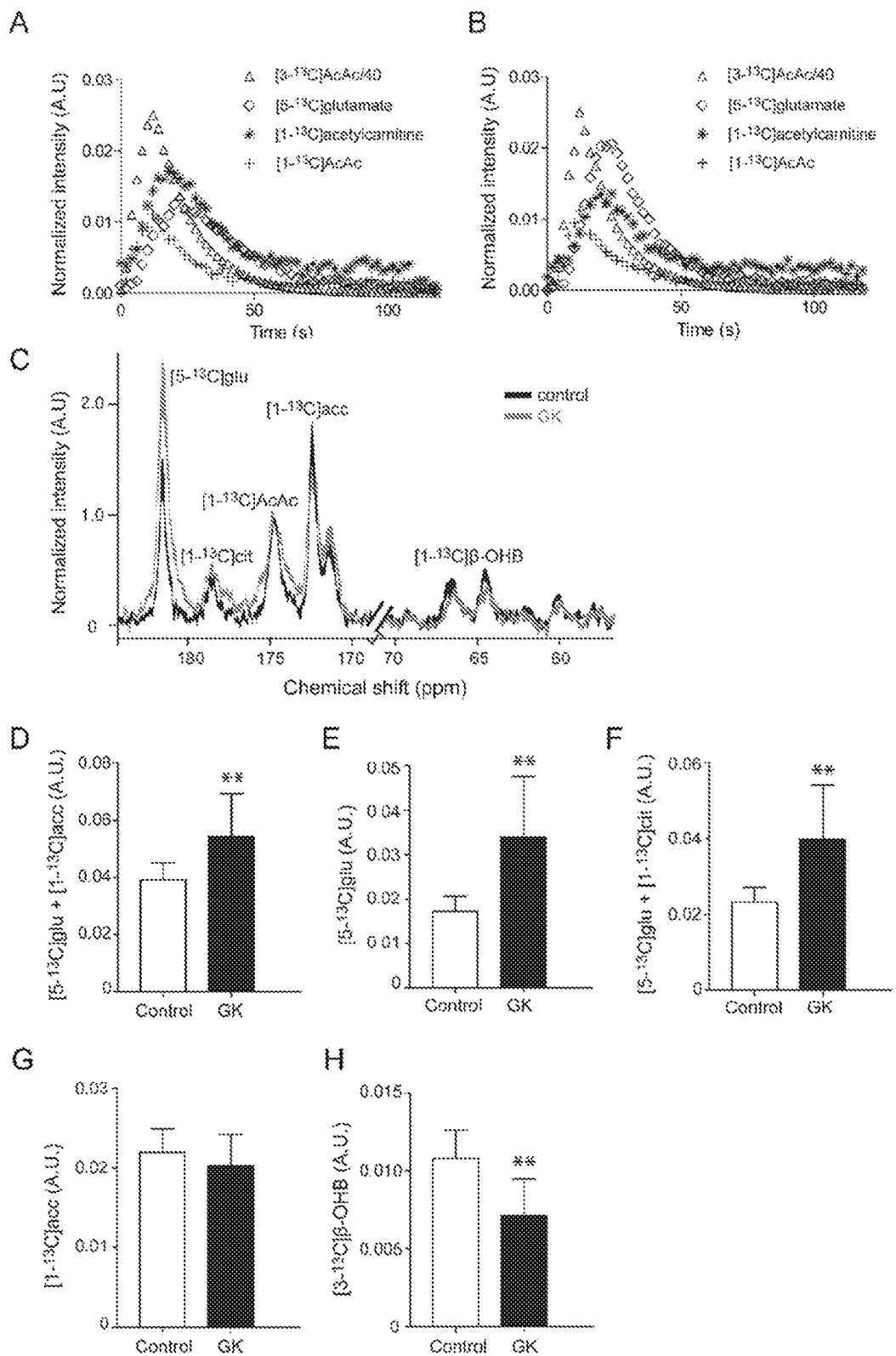
FIG. 3 shows the myocardial ketone body utilization in GK rats. The detection of [3-$^{13}$C]acetoacetate, [1-$^{13}$C]acetoacetate, [5-$^{13}$C]glutamate, and [1-$^{13}$C]acetylcarnitine over 2 minutes upon [3-$^{13}$C]acetoacetate injection in (A) controls and (B) GK rats. (C) The summed spectra over 40 seconds for control and GK rats. The thickness of the line represents SEM. The quantification of (D) [5-$^{13}$C]glutamate+[1-$^{13}$C]acetylcarnitine, (E) [5-$^{13}$C]glutamate, (F) [5-$^{13}$C]glutamate+[1-$^{13}$C]citrate, (G) [1-$^{13}$C]acetylcarnitine, and (H) [3-$^{13}$C]β-OHB. Data are means±SD (except for A-C: mean±SEM), and normalized to [3-$^{13}$C]acetoacetate (controls n=10, GK rats n=9). AcAc: acetoacetate, ace: acetylcarnitine, cit: citrate, glu: glutamate. *P<0.05, P<0.01, *P<0.001 vs. controls.

Example 3: Increased Ketone Body Utilization in Diabetic Rats as Observed by $^{13}$C MRS Upon Hyperpolarized [3-$^{13}$C]Acetoacetate Administration FIGS. 3A and 3B show the evolution of [3-$^{13}$C]acetoacetate, [5-$^{13}$C]glutamate, and [1-$^{13}$C]acetylcarnitine, and [1-$^{13}$C]acetoacetate detection, for 2 minutes immediately upon injection in control and diabetic rats, respectively. The summed spectra over 40 seconds are shown in FIG. 3C. It was observed that the total products of ketone body utilization (i.e. [5-$^{13}$C]glutamate+[1-$^{13}$C]acetylcarnitine) were higher in the diabetic rats compared with controls (P=0.009; FIG. 3D). Downstream in the ketone oxidation pathway, the production of [5-$^{13}$C]glutamate was higher in the diabetic rats than in controls (P=0.002; FIG. 3E). Glutamate presents in high equilibrium with a TCA cycle product, α-ketoglutarate, and as such, it is often used to indicate $^{13}$C carbon flow into the TCA cycle (Andrews, et al. *Am J Physiol—Regul Integr Comp Physiol.* 2009; 296:R383 LP-R393). The [1-$^{13}$C]citrate was too low for meaningful statistical comparison. Nevertheless, it was found that the total production of [5-$^{13}$C]glutamate+[1-$^{13}$C]citrate was also higher in the diabetic rats compared with controls (P=0.002; FIG. 3F). Notably, the production of [1-$^{13}$C]acetylcarnitine was similar between groups (P=0.30; FIG. 3G). Taken together, these results indicate an increased myocardial ketone body utilization in the diabetic rats, which was directed more towards oxidation in the TCA cycle, rather than incorporation into acetylcarnitine. Furthermore, the inventors were also able to detect the production of [3-$^{13}$C]β-OHB, which was lower in diabetic rats than in control rats (P=0.001; FIG. 3H).

Figure 4:
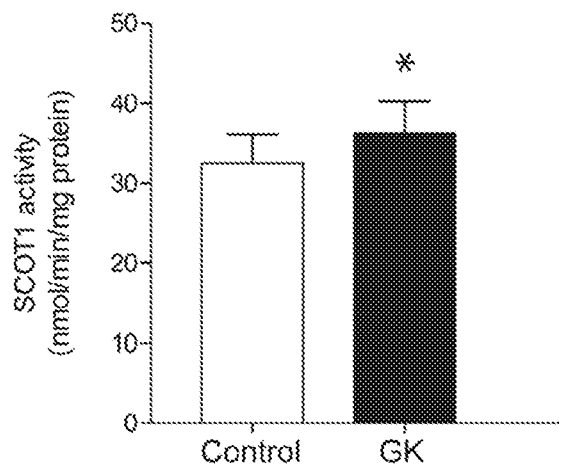
FIG. 4 shows the increased ketone body utilization in GK rats was associated with increased SCOT activity. (A) SCOT activity. Correlation between (B) SCOT activity and ([5-$^{13}$C]glutamate+[1-$^{13}$C]acetylcarnitine), and (C) between SCOT activity and [5-$^{13}$C]glutamate. Data are means±SD (controls n=10, GK rats n=9). Acc: acetylcarnitine, glu: glutamate. *P<0.05 vs. controls.
Figure 4:
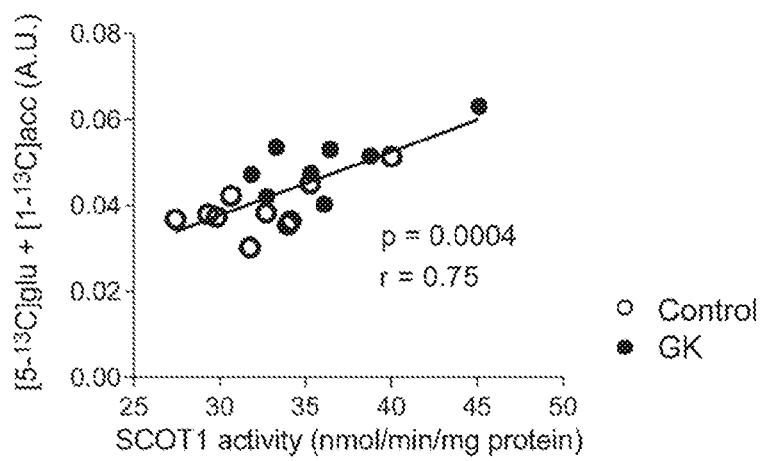
Figure 4:
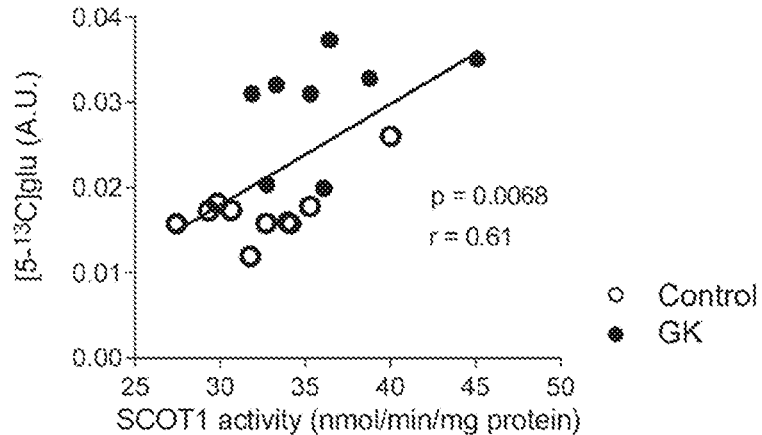

Example 4: Increased Ketone Body Utilization in Diabetic Rats Correlated with SCOT Activity It was then tested whether the increased ketone body utilization in the diabetic heart was associated with increased myocardial SCOT activity. Indeed, SCOT activity was higher in the diabetic rats compared with control (P=0.045; FIG. 4A), which is in agreement with the in vivo $^{13}$C MRS results. Furthermore, SCOT activity correlated significantly with the total of ketone body utilization products (i.e. [1-$^{13}$C]acetylcarnitine+[5-$^{13}$C]glutamate) (r=0.73, P<0.001; FIG. 4B) as well as with the product of ketone oxidation (i.e. [5-$^{13}$C]glutamate) (r=0.62; P<0.001; FIG. 4C).

Figure 5:
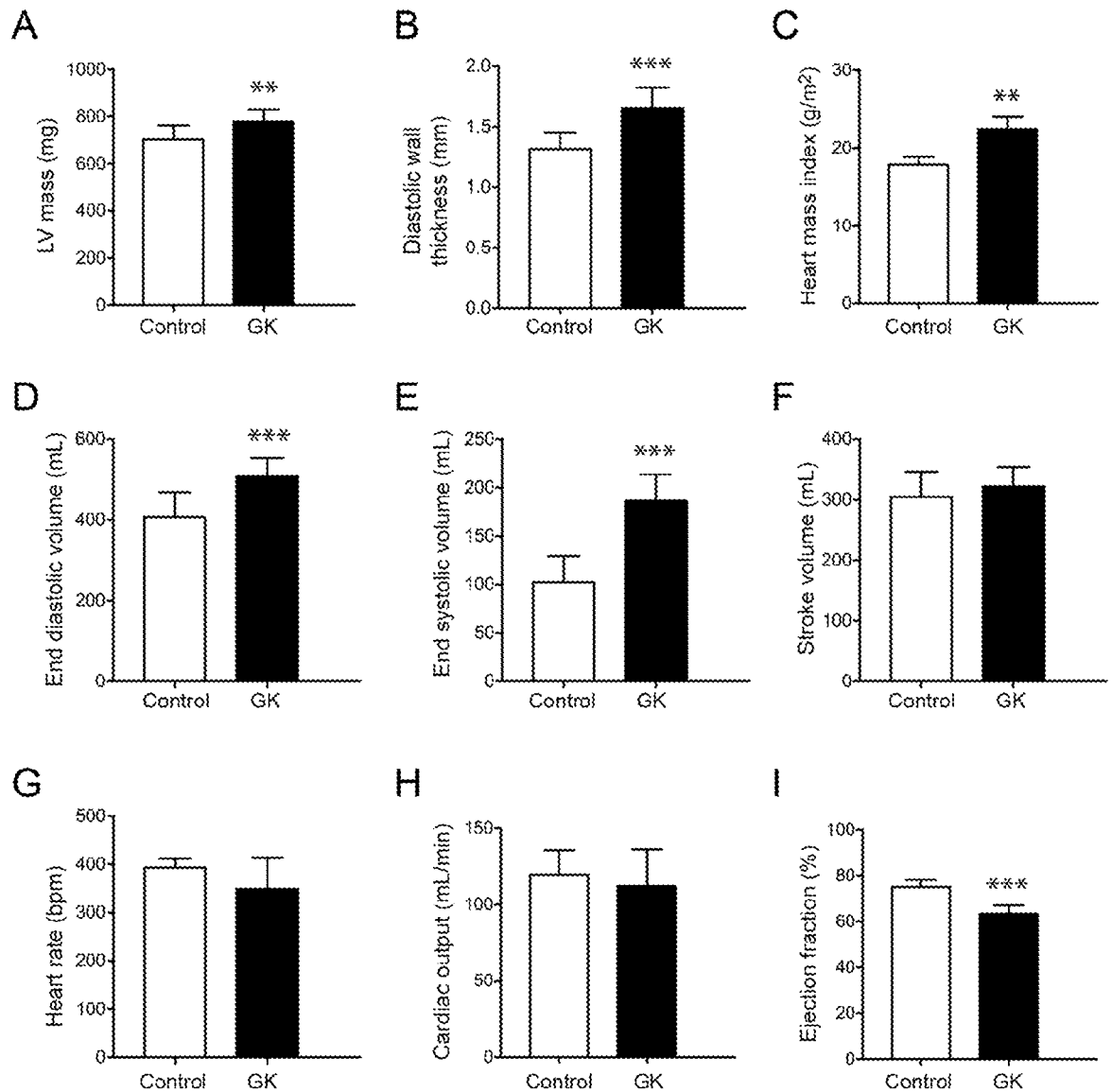
FIG. 5 shows that GK rats exhibited cardiac hypertrophy and dysfunction. (A) L V mass, (B) diastolic wall thickness, (C) heart mass index (post-mortem), (D) end diastolic volume, (E) end systolic volume, (F) stroke volume, (G) heart rate, (H) cardiac output, and (I) ejection fraction. Data are means±SD (controls n=10, GK n=9). P<0.01, *P<0.001 vs. controls.
Figure 6:
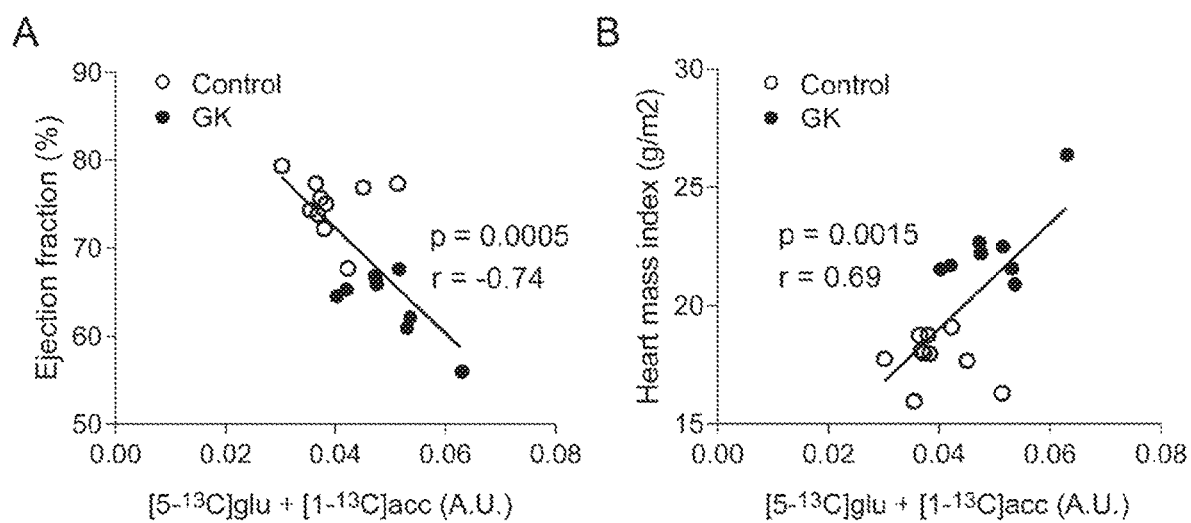
FIG. 6 shows that total of ketone body utilization products correlated with cardiac hypertrophy and function. Correlation between (A) ([5-$^{13}$C]glutamate+[1-$^{13}$C]acetylcarnitine) and cardiac function, and (B) between ([5-$^{13}$C]glutamate+[1-$^{13}$C]acetylcarnitine) and heart mass index.

Example 5: Cardiac Hypertrophy and Reduced Ejection Fraction in Diabetic Rats Correlated with Increased Ketone Body Utilization To investigate whether the modulation in cardiac metabolism in the diabetic rats was accompanied by an alteration in cardiac function, the inventors performed cinematic MRI to assess cardiac function. At 24 weeks of age, the diabetic rats exhibited increased LV mass and diastolic wall thickness (P=0.008 and P=0.0002 vs. control, respectively; FIG. 5A-B), which indicate cardiac hypertrophy. This is in agreement with the higher post-mortem heart mass index in the diabetic rats (P<0.0001 vs. control; FIG. 5C). The hypertrophy in the diabetic rats was also evidenced by higher end diastolic volume and end systolic volume (P=0.0009 and P=<0.0001 vs. control, respectively; FIG. 5D-E), while stroke volume was maintained at similar levels as controls (P=0.34; FIG. 5F). Heart rate and cardiac output were also not significantly different between diabetic rats and control rats (P=0.054 and P=0.43, respectively; Figure SG-H). Notably, ejection fraction was lower in diabetic rats than in control rats (P<0.0001; FIG. 5I). Interestingly, it was observed that the total of ketone body utilization products strongly correlated with ejection fraction (r=−0.85, P<0.0001; FIG. 6A) and with heart mass index (r=0.83, P<0.0001; FIG. 6B).

Discussion

Novelty in Measuring Myocardial Ketone Oxidation In Vivo

Myocardial ketone body metabolism has recently gained attention as studies have shown its potential relevance in nutrient-deprived (Wentz, et al. *J Biol Chem.* 2010; 285: 24447-24456), diabetes (Turko, et al. *Am J Physiol Heart Circ Physiol.* 2001; 281:H2289-94), or pathological states such as heart failure (Aubert, et al. *Circulation.* 2016; 133:698-705; Bedi, et al. *Circulation.* 2016; 133:706-716). However, it has not been possible to detect and measure in vivo ketone body utilization non-invasively in real-time with high specificity. In this work, the inventors synthesized [3-$^{13}$C]acetoacetate as a metabolic probe to study ketone metabolism in vivo using hyperpolarized $^{13}$C MRS. The detection of downstream metabolites [5-$^{13}$C]glutamate, [1-$^{13}$C]acetylcarnitine, and [1-$^{13}$C]citrate in $^{13}$C MR spectra within a minute window upon [3-$^{13}$C]acetoacetate injection provides evidence that the hyperpolarized [3-$^{13}$C]acetoacetate is taken up into the myocardium and catabolized into metabolic intermediates involved in the ATP production. In vivo, the inventors demonstrated higher $^{13}$C incorporation into [5-$^{13}$C]glutamate in the diabetic rats compared with control rats, indicating higher myocardial ketone body oxidation in the diabetic rats. This result was validated by higher activity of SCOT, the rate-limiting enzyme in ketolysis, in the myocardium tissue of diabetic rats.

Taken together, the method described herein allows the measurements of myocardial ketone body utilization non-invasively in vivo, thus it eliminates the need for biopsy or termination of animals for tissue collection at desired time points. Furthermore, [3-$^{13}$C]acetoacetate is a non-radioactive ketone substrate which can be completely metabolized by the body. As such, hyperpolarized [3-$^{13}$C]acetoacetate provides translational potential in facilitating longitudinal assessment of myocardial ketone body utilization in the diseased heart.

Insight into Ketone Metabolism in Diabetic GK Heart

The inventors demonstrated the potential of the hyperpolarized [3-$^{13}$C]acetoacetate in measuring ketone body utilization in diabetic GK rats. It is generally accepted that the rate of myocardial ketone body utilization is proportional to their availability in the heart (Bates, et al. *Biochem J.* 1968; 110:655-61; Moreno, et al. *Am J Physiol Heart Circ Physiol.* 10 2010; 298:HI556-HI564). Indeed, the inventors found that the diabetic rats had higher concentration of serum acetoacetate, which was accompanied by higher myocardial ketone oxidation, as indicated by higher incorporation of $^{13}$C label from [3-$^{13}$C]acetoacetate into a TCA cycle product [5-$^{13}$C]glutamate, compared with that in controls. Increased levels of ketone body production in the GK rats has also been reported in a previous study (Hamirani, et al. *Cardiology.* 2016; 133:157-162), as well as altered expression of genes involved in myocardial ketone metabolism (Sarkozy, et al. *Cardiovasc Diabetol.* 2016; 15:110; Devanathan, et al. *PLoS One.* 2013; 8:1-10). However, to the knowledge of the inventors, the present study is the first to report myocardial ketone oxidation in the diabetic GK rats. Additionally, the inventors were able to detect the resonances of [3-$^{13}$C]β-OHB, which could provide insights into into BDH-1 and mitochondrial redox state (Cotter, et al. *AJP Hear Circ Physiol.* 2013; 304:H1060-H1076; Williamson, et al. *Biochem J.* 1967; 103:514-527). β-OHB is the reduced form of acetoacetate, whose formation is catalyzed by mitochondrial BDH-1 and favored at equilibrium (Boc, et al. *J Biol Chem.* 1975; 250:5774-5781; Lehninger, et al. *J Biol Chem.* 1960; 235:2450-2455). Therefore, the lower [3-$^{13}$C]β-OHB/acetoacetate ratio indicates lower BDH-1 activity in the GK heart compared with controls. The formation of β-OHB is also regulated by the NAD+/NAOH ratio (Fukao, et al. *Prostaglandins, Leukot Essent Fat Acids.* 2017; 70:243-251). As β-OHB/acetoacetate ratio is inversely proportional to the NAO$^+$/NADH ratio (Williamson, et al. *Biochem J.* 1967; 103:514-527), the lower [3-$^{13}$C]β-OHB/acetoacetate ratio in the diabetic heart suggests higher mitochondrial NAO$^+$/NAOH ratio. This is in agreement with mitochondrial redox impairment generally found in diabetic heart (Aon, et al. *Antioxid Redox Signal.* 2015; 22:1563-4 1586).

Correlation Between Myocardial Ketone Body Oxidation and Cardiacfunction: is Ketone Body Oxidation Adaptive or Maladaptive?

In this study, the inventors showed that increased myocardial ketone body oxidation in the diabetic rats correlated with cardiac hypertrophy (i.e. increased cardiac index) and lower ejection fraction. This is in agreement with the findings that myocardial ketone body oxidation increased in heart failure. However, it is currently not clear whether the increase in ketone body oxidation in failing heart is an adaptive or maladaptive mechanism. A previous study showed that mice with cardiac-specific SCOT-deficiency had an exacerbated increase in LV mass and reduction in ejection fraction after 8 weeks of pressure-overload, suggesting that increased ketone oxidation may be important in heart failure settings. In agreement, a study in ischemia-reperfusion in rats showed that administration of β-OHB in fasted animals reduced myocardial infarct size and apoptosis, although myocardial ketone oxidation was not measured. More excitingly, a recent clinical trial with empagliflozin, a sodium/glucose co-transporter-2 (SGLT-2) inhibitor, showed an improved cardiovascular outcome in diabetic patients with empagliflozin treatment. An increase in plasma ketone body concentration was observed after empagliflozin treatment, leading to a hypothesis that the cardio-protective effects of empagliflozin was attributed to increased cardiac efficiency, which might be associated with increased utilization of ketone bodies as 'super fuel'. However, this 'fuel hypothesis' has recently been challenged. It has been suggested that maintained ketone body oxidation may actually cause mitochondrial protein acetylation and decreased anaplerosis, which may lead to reduced cardiac efficiency and oxidative phosphorylation, respectively. This debate remains open as data on myocardial ketone body oxidation is currently lacking, due to lack of available techniques to probe ketone body oxidation in vivo. Here, the novel method to assess myocardial ketone body utilization in vivo will be proven beneficial in the endeavor to understand ketone body metabolism.

Technical Consideration for Hyperpolarized [3-$^{13}$C]Acetoacetate Method

There are several considerations for data interpretation using this method. First, as the $^{13}$C MR spectra were acquired using surface coil localization, the hyperpolarized [3-$^{13}$C]acetoacetate and [1-$^{13}$C]acetoacetate signal were probably derived from both the myocardium and the blood pool, while [5-$^{13}$C]glutamate, [1-$^{13}$C]citrate, and [1-$^{13}$C]acetylcarnitine signals originated mainly from myocardial metabolism. Therefore, the normalization to the substrate signal (i.e. [3-$^{13}$C]acetoacetate) likely underestimated the levels of myocardial ketone oxidation. In addition, one may need to consider different contributions of blood signal for example when comparing groups with different cardiac output. In the present study, cardiac output was not different between the diabetic rats and control rats. A high-resolution $^{13}$C spectroscopic imaging may be performed to spatially resolve the signal; however, low signal-to-noise ratio (SNR) of the metabolite signals would have to be taken into consideration. Higher polarization at 5 T is an improvement that we are working on to increase the SNR.

Secondly, there may be an uptake competition between the injected hyperpolarized $^{13}$C labelled acetoacetate and the endogenous (unlabeled) acetoacetate, which may result in underestimation of ketone oxidation rate. However, since the concentration of injected acetoacetate was much higher than the endogenous acetoacetate in the blood, such uptake competition is expected to be minimal. For example, in the present study, compared with the endogenous acetoacetate concentration, the calculated acetoacetate concentration in the blood after injection was ~7 times higher (in control rats: 4.27 mM vs. 0.52 mM; GK rats: 4.30 mM vs. 0.55 mM).

Thirdly, it has been reported that at a concentration higher than 2 mM, acetoacetate infusion exerts a transient stimulatory effect on insulin secretion in man, which abates after 10-15 minutes (Balasse, et al. *Horm Metab Res.* 1970; 2:371-372). Insulin secretion may affect SCOT activity. However, the $^{13}$C MRS acquisition is only two minutes and it begins immediately upon injection of hyperpolarized acetoacetate. While the amount of insulin secreted as a result of this infusion is unknown, the effect on SCOT activity is expected to be negligible given the relatively short acquisition window. Nonetheless, it is part of future work to characterize this phenomenon.

Concluding Remarks

In this work, the inventors demonstrated the potential of hyperpolarized [3-$^{13}$C]acetoacetate in probing myocardial ketone body oxidation in vivo. It was observed that myocardial ketone oxidation was higher in diabetic rats compared with controls, which was validated with higher enzymatic activity of the rate-limiting SCOT protein. The higher myocardial ketone oxidation in diabetic rats correlated with cardiac hypertrophy and lower ejection fraction, suggesting a tight coupling between ketone body metabolism and cardiac health.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A composition comprising [3-$^{13}$C]acetoacetate, wherein at least 0.1% of said [3-$^{13}$C]acetoacetate is hyperpolarized.

2. A method of preparing [3-$^{13}$C]acetoacetate or a composition comprising the [3-$^{13}$C]acetoacetate, wherein at least 0.1% of said [3-$^{13}$C]acetoacetate is hyperpolarized, wherein the method comprises the steps of:

chemically synthesizing [3-$^{13}$C]acetoacetate or a composition comprising [3-$^{13}$C]acetoacetate; and hyperpolarizing said [3-$^{13}$C]acetoacetate or said composition.

3. The method of claim 2, wherein chemically synthesizing [3-$^{13}$C]acetoacetate comprises preparing the [3-$^{13}$C] acetoacetate from [3-$^{13}$C]ethyl acetoacetate.

4. The method of claim 3, wherein chemically synthesizing [3-$^{13}$C]acetoacetate involves saponification of [3-$^{13}$C] ethyl acetoacetate.

5. The method of claim 2, wherein chemically synthesizing [3-$^{13}$C]acetoacetate comprises reacting [3-$^{13}$C]ethyl acetoacetate and a base under conditions allowing said reaction.

6. The method of claim 2, wherein hyperpolarizing the chemically synthesized [3-$^{13}$C]acetoacetate comprises subjecting the chemically synthesized [3-$^{13}$C]acetoacetate to Dynamic Nuclear Polarization (DNP).

7. A method of determining spatial and temporal distribution and metabolism of [3-$^{13}$C]acetoacetate and/or its metabolites in a cell or a subject, wherein the method comprises the steps of:

administering the [3-$^{13}$C]acetoacetate or a composition comprising the [3-$^{13}$C]acetoacetate to the cell or subject, wherein at least 0.1% of said [3-$^{13}$C]acetoacetate is hyperpolarized; and determining the spatial and temporal distribution and metabolism of hyperpolarized [3-$^{13}$C]acetoacetate and/or its metabolites in the cell or subject by magnetic resonance imaging (MRI), magnetic resonance spectroscopy (MRS), and/or magnetic resonance spectroscopic imaging (MRSI).

8. The method of claim 7, wherein the cell or subject is a cell culture, an ex vivo tissue, a human, or an animal.

9. The method of claim 7, wherein the metabolites of [3-$^{13}$C]acetoacetate are selected from the group consisting of [5-$^{13}$C]glutamate, [1-$^{13}$C]citrate, [1-$^{13}$C]acetylcarnitine, and [3-$^{13}$C]beta-hydroxybutyrate.

10. The method of claim 7, wherein magnetic resonance signals from the hyperpolarized [3-$^{13}$C]acetoacetate and its metabolites are used to study in vivo metabolism of acetoacetate and/or other ketone bodies.

11. The method of claim 7, wherein magnetic resonance signals from the hyperpolarized [3-$^{13}$C]acetoacetate and its metabolites are used to quantify specific physiological functions of the cell or subject in healthy and/or diseased conditions.

12. The method of claim 7, wherein magnetic resonance signals from the hyperpolarized [3-$^{13}$C]acetoacetate and its metabolites are used to diagnose a condition, disease, or disorder associated with the metabolism of acetoacetate and/or other ketone bodies.

13. The method of claim 12, wherein the condition, disease, or disorder is a cancer, diabetes, cardiovascular disease, or neurodegenerative disease.

* * * * *